United States Patent
Halasa et al.

(10) Patent No.: US 9,587,060 B2
(45) Date of Patent: Mar. 7, 2017

(54) FUNCTIONALIZED RUBBERY POLYMERS

(75) Inventors: Adel Farhan Halasa, Bath, OH (US); Wen-Liang Hsu, Cuyahoga Falls, OH (US); Jin-Ping Zhou, Bartlesville, OK (US); Teresa Diane Martter, Akron, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 691 days.

(21) Appl. No.: 11/603,719

(22) Filed: Nov. 22, 2006

(65) Prior Publication Data
US 2007/0123631 A1 May 31, 2007

Related U.S. Application Data

(60) Provisional application No. 60/741,023, filed on Nov. 30, 2005.

(51) Int. Cl.
| | | |
|---|---|---|
| C08F 236/10 | (2006.01) | |
| C08F 236/12 | (2006.01) | |
| C08F 212/08 | (2006.01) | |
| C08F 212/14 | (2006.01) | |
| C08K 5/548 | (2006.01) | |
| C08K 3/36 | (2006.01) | |
| B60C 1/00 | (2006.01) | |
| C07C 211/27 | (2006.01) | |
| C07F 7/10 | (2006.01) | |
| C08L 21/00 | (2006.01) | |
| C08L 97/00 | (2006.01) | |

(52) U.S. Cl.
CPC .......... *C08F 236/12* (2013.01); *B60C 1/0016* (2013.04); *C07C 211/27* (2013.01); *C07F 7/10* (2013.01); *C08F 212/08* (2013.01); *C08F 212/14* (2013.01); *C08F 236/10* (2013.01); *C08K 3/36* (2013.01); *C08K 5/548* (2013.01); *C08L 21/00* (2013.01); *C08L 97/00* (2013.01)

(58) Field of Classification Search
CPC .... C08F 236/10; C08F 236/12; C08F 212/08; C08F 212/14
USPC ........................................................ 526/310
See application file for complete search history.

(56) References Cited

U.S. PATENT DOCUMENTS

| | | | | |
|---|---|---|---|---|
| 4,471,079 A * | 9/1984 | Enami | ............................ | 523/161 |
| 4,614,771 A * | 9/1986 | Watanabe | ............... | C08C 19/44 525/332.7 |
| 4,935,471 A | 6/1990 | Halasa et al. | .................. | 525/359 |
| 5,332,810 A * | 7/1994 | Lawson et al. | ............... | 540/450 |
| 5,932,662 A | 8/1999 | Lawson et al. | ............... | 525/280 |
| 6,080,835 A | 6/2000 | Lawson et al. | ............... | 528/396 |
| 6,084,025 A | 7/2000 | Kitamura et al. | ............ | 524/575 |
| 6,191,234 B1 * | 2/2001 | Tadaki et al. | ............... | 525/332.9 |
| 6,344,538 B1 | 2/2002 | Sheares | ........................ | 528/396 |
| 6,812,307 B2 | 11/2004 | Halasa et al. | ................. | 526/173 |
| 7,091,274 B2 * | 8/2006 | Thielen et al. | ............... | 524/496 |

FOREIGN PATENT DOCUMENTS

JP 57034106 A * 2/1982

OTHER PUBLICATIONS

Keilen and Pollak (Lignin for Reinforcing Rubber. Industrial and Engineering Chemistry. Apr. 1947. p. 480-483).*
CAPlus Accession No. 1982:407926. Abstract for JP 57034106 A.*

* cited by examiner

*Primary Examiner* — Brieann R Fink
(74) *Attorney, Agent, or Firm* — Alvin T. Rockhill

(57) ABSTRACT

This invention discloses a process for the synthesis of a rubbery polymer by emulsion polymerization that comprised polymerizing (1) a conjugated diolefin monomer and (2) a functionalized monomer having the structural formula:

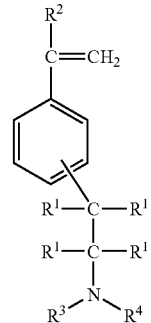

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom, wherein said polymerization is conducted in an aqueous medium, and wherein said polymerization is initiated with a free radical initiator.

10 Claims, No Drawings

FUNCTIONALIZED RUBBERY POLYMERS

This application claims benefit of U.S. Provisional Patent Application Ser. No. 60/741,023, filed on Nov. 30, 2005. The teachings of U.S. Provisional Patent Application Ser. No. 60/741,023 are incorporated herein by reference in their entirety.

BACKGROUND OF THE INVENTION

It is important for rubbery polymers that are used in tires, hoses, power transmission belts and other industrial products to have good compatibility with fillers, such as carbon black and silica. To attain improved interaction with fillers such rubbery polymers can be functionalized with various compounds, such as amines. U.S. Pat. No. 4,935,471 discloses a process for preparing a polydiene having a high level of affinity for carbon black which comprises reacting a metal terminated polydiene with a capping agent selected from the group consisting of (a) halogenated nitriles having the structural formula X-A-C≡N, wherein X represents a halogen atom and wherein A represents an alkylene group containing from 1 to 20 carbon atoms, (b) heterocyclic aromatic nitrogen containing compounds, and (c) alkyl benzoates. The capping agents disclosed by U.S. Pat. No. 4,935,471 react with metal terminated polydienes and replace the metal with a terminal cyanide group, a heterocyclic aromatic nitrogen containing group or a terminal group which is derived from an alkyl benzoate. For example, if the metal terminated polydiene is capped with a nitrile, it will result in the polydiene chains being terminated with cyanide groups. The use of heterocyclic aromatic nitrogen containing compounds as capping agents can result in the polydiene chains being terminated with a pyrrolyl group, an imidazolyl group, a pyrazolyl group, a pyridyl group, a pyrazinyl group, a pyrimidinyl group, a pyridazinyl group, an indolizinyl group, an isoindolyl group, a 3-H-indolyl group, a cinnolinyl group, a pyridinyl group, a .beta.-carbolinyl group, a perimidinyl group, a phenanthrolinyl group or the like.

U.S. Pat. No. 4,935,471 also discloses that lithium amides are highly preferred initiators because they can be used to prepare polydienes which are terminated with polar groups at both ends of their polymer chains. The extra polar functionality provided by lithium amides results in increased interaction with carbon black resulting in better polymer-carbon black dispersion. The lithium amides disclosed by U.S. Pat. No. 4,935,471 include lithium pyrrolidide. U.S. Pat. No. 4,935,471 also indicates that preferred initiators include amino alkyl lithium compounds of the structural formula:

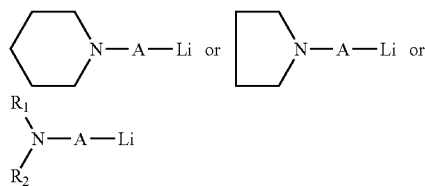

wherein A represents an alkylene group containing from 1 to 20 carbon atoms, and wherein $R_1$ and $R_2$ can be the same or different and represent alkyl groups containing from 1 to 20 carbon atoms.

It is also desirable for synthetic rubbers to exhibit low levels of hysteresis. This is particularly important in the case of rubbers that are used in tire tread compounds. Such polymers are normally compounded with sulfur, carbon black, accelerators, antidegradants and other desired rubber chemicals and are then subsequently vulcanized or cured into the form of a useful article. It has been established that the physical properties of such cured rubbers depend upon the degree to which the carbon black is homogeneously dispersed throughout the polydiene rubber. This is in turn related to the level of affinity that carbon black has for the rubber. This can be of practical importance in improving the physical characteristics of rubber articles that are made utilizing polydiene rubbers. For example, the rolling resistance and tread wear characteristics of tires can be improved by increasing the affinity of carbon black to the rubbery polymers utilized therein. Therefore, it would be highly desirable to improve the affinity of a given polydiene rubber for carbon black and/or silica. This is because a better dispersion of carbon black throughout polydiene rubbers which are utilized in compounding tire tread compositions results in a lower hysteresis value and consequently tires made therefrom have lower rolling resistance. It is also known that a major source of hysteresis is due to polymer chain ends that are not capable of full elastic recovery. Accordingly, improving the affinity of the rubber chain ends to the filler is extremely important in reducing hysteresis.

U.S. Pat. No. 6,080,835 discloses a functionalized elastomer comprising: a functional group defined by the formula:

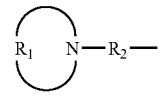

where $R_1$ is a selected from the group consisting of a divalent alkylene group, an oxy-alkylene group, an amino alkylene group, and a substituted alkylene group, each group having from about 6 to about 20 carbon atoms, $R_2$ is covalently bonded to the elastomer and is selected from the group consisting of a linear-alkylene group, a branched-alkylene group, and a cyclo-alkylene group, each group having from about 2 to about 20 carbon atoms.

U.S. Pat. No. 5,932,662 discloses a method of preparing a polymer comprising: preparing a solution of one or more anionically polymerizable monomers in a solvent; and, polymerizing under effective conditions, said monomers in the presence of a polymerization initiator having the formula

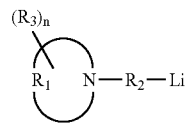

wherein $R_1$ is a divalent alkylene, an oxy- or amino-alkylene having from 6 to about 20 carbon atoms; and, $R_2$ is a linear-alkylene, branched-alkylene, or cyclo-alkylene having from about 2 to about 20 carbon atoms, Li is a lithium atom bonded directly to a carbon atom of $R_2$; and $R_3$ is a tertiary amino, an alkyl having from about 1 to about 12 carbon atoms; an aryl having from about 6 to about 20 carbon atoms; an alkaryl having from about 7 to about 20 carbon atoms; an alkenyl having from about 2 to about 12 carbon atoms; a cycloalkyl having from about 5 to about 20 carbon atoms; a cycloalkenyl having from about 5 to about 20 carbon atoms; a bicycloalkyl having from about 6 to about 20 carbon atoms; and, a bicycloalkenyl having from about 6 to about 20 carbon atoms; where n is an integer of from 0 to about 10.

U.S. Pat. No. 6,084,025 discloses a functionalized polymer prepared by a process comprising the steps of: preparing a solution of a cyclic amine compound, an organolithium compound, and from 3 to about 300 equivalents, based upon one equivalent of lithium, of a monomer selected from vinyl aromatic monomers, and mixtures thereof, where said cyclic amine compound is defined by the formula

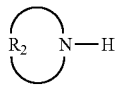

where $R_2$ is selected from the group consisting of an alkylene, substituted alkylene, bicycloalkane, and oxy- or N-alkylamino-alkylene group having from about 3 to about 16 methylene groups, N is a nitrogen atom, and H is a hydrogen atom, thereby forming a polymerization initiator having the formula $A(SOL)_y Li$, where Li is a lithium atom, SOL is a divalent hydrocarbon group having from 3 to about 300 polymerized monomeric units, y is from 0.5 to about 3, and A is a cyclic amine radical derived from said cyclic amine; charging the solution containing $A(SOL)_y Li$ with from about 0.01 to about 2 equivalents per equivalent of lithium of a chelating reagent, and an organic alkali metal compound selected from compounds having the formula $R_4 OM$, $R_5 C(O)OM$, $R_6 R_7 NM$, and $R_8 SO_3 M$, where $R_4$, $R_5$, $R_6$, $R_7$, and $R_8$ are each selected from alkyls, cycloalkyls, alkenyls, aryls, or phenyls, having from 1 to about 12 carbon atoms; and where M is Na, K, Rb or Cs, and sufficient monomer to form a living polymeric structure; and quenching the living polymeric structure.

In the initiator systems of U.S. Pat. No. 6,084,025 a chelating reagent can be employed to help prevent heterogeneous polymerization. The reagents that are reported as being useful include tetramethylethylenediamine (TMEDA), oxolanyl cyclic acetals, and cyclic oligomeric oxolanyl alkanes. The oligomeric oxolanyl alkanes may be represented by the structural formula:

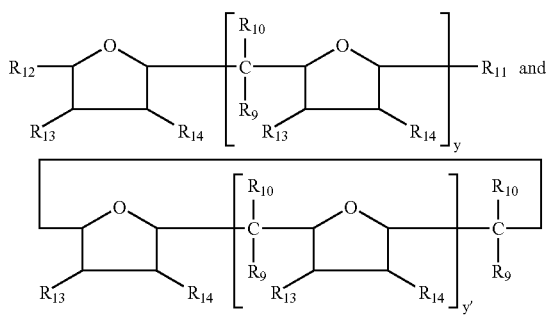

wherein $R_9$ and $R_{10}$ independently are hydrogen or an alkyl group and the total number of carbon atoms in $-CR_9R_{10}-$ ranges between one and nine inclusive; y is an integer of 1 to 5 inclusive; y' is an integer of 3 to 5 inclusive; and $R_{11}$, $R_{12}$, $R_{13}$, and $R_{14}$ independently are $-H$ or $-C_nH_{2n+1}$, wherein n=1 to 6.

U.S. Pat. No. 6,344,538 discloses functionalized monomers and polymerized functionalized monomers selected from the group consisting of 2-(N,N-dimethylaminomethyl)-1,3-butadiene, 2-(N,N-diethylaminomethyl)-1,3-butadiene, 2-(N,N-di-n-propylaminomethyl)-1,3-butadiene, 2-(cyanomethyl)-1,3-butadiene, 2-(aminomethyl)-1,3-butadiene, 2-(hydroxymethyl)-1,3-butadiene, 2-(carboxymethy)-1,3-butadiene, 2-(acetoxymethyl)-1,3-butadiene, 2-(2-alkoxy-2-oxoethyl)-1,3-butadiene, 2,3-bis(cyanomethyl)-1,3-butadiene, 2,3-bis(dialkylaminomethyl)-1,3-butadiene, 2,3-bis(4-ethoxy-4-4-oxobutyl)-1,3-butadiene and 2,3-bis(3-cyanopropyl)-1,3-butadiene, and methods for preparing such functionalized diene monomers and polymers.

U.S. Pat. No. 6,812,307 discloses that random copolymers of 1,3-butadiene monomer and 3-(2-pyrrolidinoethyl) styrene and/or 4-(2-pyrrolidinoethyl) styrene having a low vinyl content can be synthesized by anionic polymerization at normal polymerization temperatures without the need for a conventional polar modifier. U.S. Pat. No. 6,812,307 more specifically discloses a process for synthesizing a rubbery polymer that comprises copolymerizing at least one conjugated diolefin monomer and at least one functionalized monomer in an organic solvent at a temperature which is within the range of 20° C. to about 100° C., wherein the polymerization is initiated with an anionic initiator, wherein the functionalized monomer is of the structural formula:

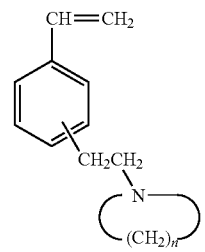

wherein n represents an integer from 4 to about 10, and wherein the polymerization is conducted in the absence of conventional polar modifiers.

SUMMARY OF THE INVENTION

The present invention relates to functionalized monomers that can be polymerized into rubbery polymers having low hysteresis and good compatibility with fillers, such as carbon black and silica. The functionalized monomers of this invention are typically incorporated into the rubbery polymer by being copolymerized with one or more conjugated diolefin monomers and optionally other monomers that are copolymerizable therewith, such as vinyl aromatic monomers. In any case, improved polymer properties are realized because the functionalized monomers of this invention improve the compatibility of the rubber with the types of fillers that are typically used in rubber compounds, such as carbon black and silica.

This invention more specifically discloses monomers that are particularly useful for copolymerization with conjugated diolefin monomers to produce rubbery polymers having better compatibility with fillers. The monomers of this invention have a structural formula selected from the group consisting of

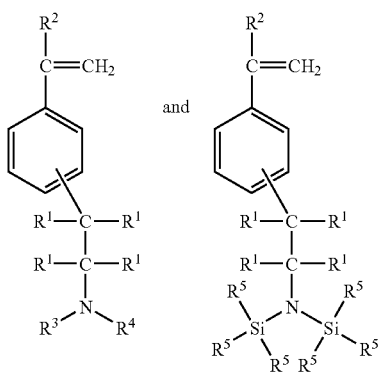

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom, and wherein the $R^5$ groups can be the same or different and represent alkyl groups containing from 1 to about 8 carbon atoms.

The present invention discloses a process for the synthesis of a rubbery polymer by emulsion polymerization that comprised polymerizing (1) a conjugated diolefin monomer and (2) a functionalized monomer having the structural formula:

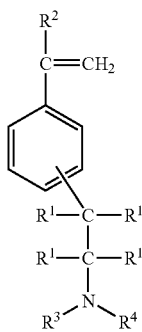

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom, wherein said polymerization is conducted in an aqueous medium, and wherein said polymerization is initiated with a free radical initiator.

The present invention further discloses a process for the synthesis of a rubbery polymer by anionic polymerization that comprised polymerizing (1) a conjugated diolefin monomer and (2) a functionalized monomer having the structural formula:

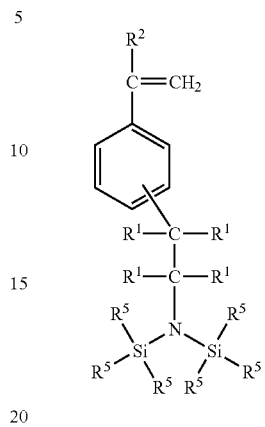

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein the $R^5$ groups can be the same or different and represent alkyl groups containing from 1 to about 8 carbon atoms, wherein said polymerization is conducted in an organic solvent, and wherein said polymerization is initiated with an anionic initiator.

The present invention further discloses a polymer which is comprised of repeat units that are derived from (1) a conjugated diolefin monomer and (2) a functionalized monomer having the structural formula:

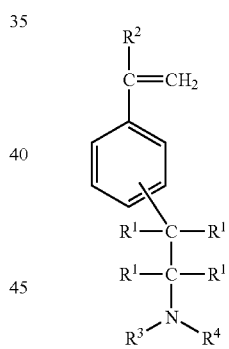

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom.

The present invention further discloses a rubbery composition which is comprised of (A) a silica filler, (B) optionally, a silica coupling agent, wherein the silica coupling agent is present at a maximum level of less than 5 phr, and (C) a rubbery polymer which is comprised of repeat units that are derived from (1) at least one conjugated diolefin monomer, and (2) a functionalized monomer having the structural formula:

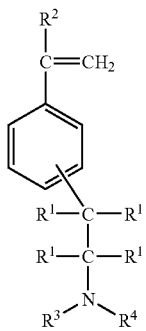

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom.

The present invention further discloses a tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is comprised of (I) a filler, and (II) a rubbery composition which is comprised of (A) a silica filler, (B) optionally, a silica coupling agent, wherein the silica coupling agent is present at a maximum level of less than 5 phr, and (C) a rubbery polymer which is comprised of repeat units that are derived from (1) at least one conjugated diolefin monomer, and (2) a functionalized monomer having the structural formula:

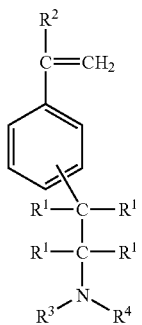

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom.

DETAILED DESCRIPTION OF THE INVENTION

The functionalized monomers of this invention can be copolymerized into virtually any type of synthetic rubber. In most cases the functionalized monomer will be copolymerized with at least one conjugated diolefin monomer. Optionally, other monomers that are copolymerizable with conjugated diolefin monomers, such as vinyl aromatic monomers, can also be included in the polymerization. In any case, typically from about 0.1 phm (parts by weight by 100 parts by weight of monomers) to about 100 phm of the functionalized monomer will be included in the polymerization. More typically, from about 0.05 phm to about 10 phm of the functionalized monomer will be included in the rubbery polymer. Good results can normally be attained by including 0.1 phm to 5 phm of the functionalized monomer in the rubbery polymer. Most typically, the functionalized monomer will be incorporated into the rubbery polymer at a level which is within the range of 0.5 phm to 2 phm.

According to this invention, polymerization and recovery of polymers are suitably carried out according to various methods suitable for diene monomer polymerization processes. This includes batchwise, semi-continuous, or continuous operations. The polymerization of the functionalized monomers of the invention may also be carried out in a number of different polymerization reactor systems, including but not limited to bulk polymerization, vapor phase polymerization, solution polymerization, suspension polymerization, emulsion polymerization, and precipitation polymerization systems. Free radical emulsion polymerization techniques are typically utilized in the polymerization of monomers of this invention having the structural formula:

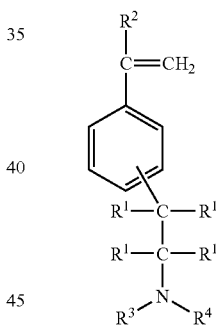

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom. Monomers of this type are typically polymerized utilizing free radical initiators under emulsion polymerization conditions by virtue of the fact that they cannot be polymerized by solution polymerization utilizing anionic initiators, such as alkyl lithium compounds.

Solution polymerizations that are initiated with anionic initiators or emulsion polymerizations that are initiated with free radical initiators can be used to polymerize monomers of the structural formula

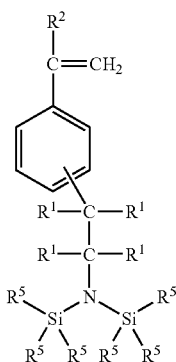

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein the $R^5$ groups can be the same or different and represent alkyl groups containing from 1 to about 8 carbon atoms, wherein said polymerization is conducted in an organic solvent, and wherein said polymerization is initiated with an anionic initiator.

Depending upon the monomer the polymerization reaction may use a free radical initiator, a redox initiator, an anionic initiator, a cationic initiator, or a Zeigler-Natta catalyst system. The preferred initiation system depends upon the particular monomers being polymerized and the desired characteristics of the rubbery polymer being synthesized. In emulsion polymerizations free radical initiators are typically utilized. In solution polymerizations Zeigler-Natta catalyst systems or anionic initiators, such as alkyl lithium compounds, are typically employed to initiate the polymerization. An advantage of free radical polymerization is that reactions can typically be carried out under less rigorous conditions than ionic polymerizations. Free radical initiation systems also exhibit a greater tolerance of trace impurities.

Examples of free radical initiators that are useful in the practice of the present invention are those known as "redox" initiators, such as combinations of chelated iron salts, sodium formaldehyde sulfoxylate, and organic hydroperoxides. Representative of organic hydroperoxides are cumene hydroperoxide, paramenthane hydroperoxide, and tertiary butyl hydroperoxide. Tertiary butyl hydroperoxide (t-BHP), tertiary butyl peracetate (t-BPA) and "azo" initiators, such as azobisiobutyronitrile (AIBN), are preferred.

The reaction temperature is typically maintained in the range of 0° C. to 150° C. Temperatures between about 20 and 80° C. are generally preferred. The reaction pressure is not critical. It is typically only sufficiently high to maintain liquid phase reaction conditions; it may be autogenic pressure, which will vary depending upon the components of the reaction mixture and the temperature, or it may be higher, e.g., up to 1000 psi.

In batch operations, the polymerization time of functionalized diene monomers can be varied as desired; it may vary, for example, from a few minutes to several days. Polymerization in batch processes may be terminated when monomer is no longer absorbed, or earlier, if desired, e.g., if the reaction mixture becomes too viscous. In continuous operations, the polymerization mixture may be passed through a reactor of any suitable design. The polymerization reactions in such cases are suitably adjusted by varying the residence time. Residence times vary with the type of reactor system and range, for example, from 10 to 15 minutes to 24 or more hours.

The concentration of monomer in the reaction mixture may vary upward from 5 percent by weight of the reaction mixture, depending on the conditions employed; the range from 20 to 80 percent by weight is preferred.

The polymerization reactions according to this invention may be carried out in a suitable solvent that is liquid under the conditions of reaction and relatively inert. The solvent may have the same number of carbon atoms per molecule as the diene reactant or it may be in a different boiling range. Preferred solvents are alkane and cycloalkane hydrocarbons. Suitable solvents are, for example, hexane, cyclohexane, methylcyclohexane, or various saturated hydrocarbon mixtures. Aromatic hydrocarbons such as benzene, toluene, isopropylbenzene, xylene, or halogenated aromatic compounds such as chlorobenzene, bromobenzene, or orthodichlorobenzene may also be employed. Other useful solvents include tetrahydrofuran and dioxane.

Conventional emulsion recipes may also be employed with the present invention; however, some restrictions and modifications may arise either from the polymerizable monomer itself, or the polymerization parameters. Ionic surfactants, known in the art, including sulfonate detergents and carboxylate, sulfate, and phosphate soaps are useful in this invention. The level of ionic surfactant is computed based upon the total weight of the organic components and may range from about 2 to 30 parts by weight of ionic surfactant per 100 parts by weight of organic components.

Preferably the polymerization is carried out to complete functionalized diene monomer conversion in order to incorporate essentially all of the polymerizable functional group-bearing monomer. Incremental addition, or a chain transfer agent, may be used in order to avoid excessive gel formation. Such minor modifications are within the skill of the artisan. After the polymerization is complete, the polymer is recovered from a slurry or solution of the polymer. A simple filtration may be adequate to separate polymer from diluent. Other means for separating polymer from diluent may be employed. The polymer may be treated, separately or while slurried in the reaction mixture, in order to separate residues. Such treatment may be with alcohols such as methanol, ethanol, or isopropanol, with acidified alcohols, or with other similar polar liquids. In many cases the polymers are obtained in hydrocarbon solutions and the polymer can be recovered by coagulation with acidified alcohol, e.g., rapidly stirred methanol or isopropanol containing 2% hydrochloric acid. Following this initial coagulation, the polymers may be washed several more times in methanol.

The functionalized diene monomers according to the present invention may also be polymerized with one or more comonomers. Some adjustments in the polymerization recipe or reaction conditions may be necessary to obtain a satisfactory rate of polymer formation, depending on the amount of functionalized monomer included and the other monomers involved. Examples of comonomers that are useful in the practice of this invention are diene monomers such as butadiene, isoprene, and hexadienes. One may, in addition to the diene monomers, use a vinyl monomer such as styrene, α-methylstyrene, divinyl benzene, vinyl chloride, vinyl acetate, vinylidene chloride, methyl methacrylate, ethyl acrylate, vinylpyridine, acrylonitrile, methacrylonitrile, methacrylic acid, itaconic acid and acrylic acid. Mixtures of different functionalized monomers and mixtures of different comonomers may be used. The monomer charge ratio by weight is normally from about 0.10/99.9 to 99.9/

0.10 functionalized monomer to comonomer (including any additional vinyl monomer). A charge ratio by weight of about 5/95 to about 80/20 is preferred with 10/90 to 40/60 the most preferred. According to one embodiment, the weight ratio of functionalized diene monomer to diene monomer to vinyl monomer may range from 5:75:20 to 95:5:0. Ratios will vary depending on the amount of chemical functionality desired to be incorporated and on the reactivity ratios of the monomers in the particular polymerization system used.

The functionalized monomers of this invention offer a unique ability to randomly copolymerize with conjugated diolefin monomers in solution polymerizations that are conducted at temperatures of 20° C. or higher. The functionalized monomers of this invention can be incorporated into virtually any type of rubbery polymer that is capable of being made by solution polymerization with an anionic initiator or Zeigler-Natta type of catalyst. The polymerization employed in synthesizing the rubbery polymers will normally be carried out in a hydrocarbon solvent. Such hydrocarbon solvents are comprised of one or more aromatic, paraffinic or cycloparaffinic compounds. These solvents will normally contain from about 4 to about 10 carbon atoms per molecule and will be liquid under the conditions of the polymerization. Some representative examples of suitable organic solvents include pentane, isooctane, cyclohexane, methylcyclohexane, isohexane, n-heptane, n-octane, n-hexane, benzene, toluene, xylene, ethylbenzene, diethylbenzene, isobutylbenzene, petroleum ether, kerosene, petroleum spirits, petroleum naphtha, and the like, alone or in admixture.

In the solution polymerization, there will normally be from 5 to 30 weight percent monomers in the polymerization medium. Such polymerization media are, of course, comprised of the organic solvent and monomers. In most cases, it will be preferred for the polymerization medium to contain from 10 to 25 weight percent monomers. It is generally more preferred for the polymerization medium to contain 15 to 20 weight percent monomers.

The synthetic rubbers made by the process of this invention can be made by random copolymerization of the functionalized monomer with a conjugated diolefin monomer or by the random terpolymerization of the functionalized monomer with a conjugated diolefin monomer and a vinyl aromatic monomer. It is, of course, also possible to make such rubbery polymers by polymerizing a mixture of conjugated diolefin monomers with one or more ethylenically unsaturated monomers, such as vinyl aromatic monomers. The conjugated diolefin monomers which can be utilized in the synthesis of rubbery polymers which can be coupled in accordance with this invention generally contain from 4 to 12 carbon atoms. Those containing from 4 to 8 carbon atoms are generally preferred for commercial purposes. For similar reasons, 1,3-butadiene and isoprene are the most commonly utilized conjugated diolefin monomers. Some additional conjugated diolefin monomers that can be utilized include 2,3-dimethyl-1,3-butadiene, piperylene, 3-butyl-1,3-octadiene, 2-phenyl-1,3-butadiene, and the like, alone or in admixture.

Some representative examples of ethylenically unsaturated monomers that can potentially be polymerized into rubbery polymers that contain the functionalized monomers of this invention include alkyl acrylates, such as methyl acrylate, ethyl acrylate, butyl acrylate, methyl methacrylate and the like; vinylidene monomers having one or more terminal $CH_2=CH-$ groups; vinyl aromatics such as styrene, α-methylstyrene, bromostyrene, chlorostyrene, fluorostyrene and the like; α-olefins such as ethylene, propylene, 1-butene and the like; vinyl halides, such as vinylbromide, chloroethane (vinylchloride), vinylfluoride, vinyliodide, 1,2-dibromoethene, 1,1-dichloroethene (vinylidene chloride), 1,2-dichloroethene and the like; vinyl esters, such as vinyl acetate; α,β-olefinically unsaturated nitriles, such as acrylonitrile and methacrylonitrile; α,β-olefinically unsaturated amides, such as acrylamide, N-methyl acrylamide, N,N-dimethylacrylamide, methacrylamide and the like.

Rubbery polymers which are copolymers of one or more diene monomers with one or more other ethylenically unsaturated monomers will normally contain from about 50 weight percent to about 99 weight percent conjugated diolefin monomers and from about 1 weight percent to about 50 weight percent of the other ethylenically unsaturated monomers in addition to the conjugated diolefin monomers. For example, copolymers of conjugated diolefin monomers with vinylaromatic monomers, such as styrene-butadiene rubbers which contain from 50 to 95 weight percent conjugated diolefin monomers and from 5 to 50 weight percent vinylaromatic monomers, are useful in many applications.

Vinyl aromatic monomers are probably the most important group of ethylenically unsaturated monomers which are commonly incorporated into polydiene rubbers. Such vinyl aromatic monomers are, of course, selected so as to be copolymerizable with the conjugated diolefin monomers being utilized. Generally, any vinyl aromatic monomer which is known to polymerize with organolithium initiators can be used. Such vinyl aromatic monomers typically contain from 8 to 20 carbon atoms. Usually, the vinyl aromatic monomer will contain from 8 to 14 carbon atoms. The most widely used vinyl aromatic monomer is styrene. Some examples of vinyl aromatic monomers that can be utilized include styrene, 1-vinylnaphthalene, 2-vinylnaphthalene, α-methylstyrene, 4-phenylstyrene, 3-methylstyrene and the like.

Some representative examples of rubbery polymers that can be functionalized with the functionalized monomers of this invention include polybutadiene homopolymer, polyisoprene homopolymer, styrene-butadiene rubber (SBR), α-methylstyrene-butadiene rubber, α-methylstyrene-isoprene rubber, styrene-isoprene-butadiene rubber (SIBR), styrene-isoprene rubber (SIR), isoprene-butadiene rubber (IBR), α-methylstyrene-isoprene-butadiene rubber and α-methylstyrene-styrene-isoprene-butadiene rubber. In cases where the rubbery polymer is comprised of repeat units that are derived from two or more monomers, the repeat units which are derived from the different monomers, including the functionalized monomers, will normally be distributed in an essentially random manner. The repeat units that are derived from the monomers differ from the monomer in that a double bond is normally consumed in by the polymerization reaction.

The rubbery polymer can be made by solution polymerization in a batch process or by a continuous process by continuously charging at least one conjugated diolefin monomer, the functionalized monomer, and any additional monomers into a polymerization zone. The polymerization zone will typically be a polymerization reactor or a series of polymerization reactors. The polymerization zone will normally provide agitation to keep the monomers, polymer, initiator, and modifier well dispersed throughout the organic solvent the polymerization zone. Such continuous polymerizations are typically conducted in a multiple reactor system. The rubbery polymer synthesized is continuously withdrawn from the polymerization zone. The monomer conversion attained in the polymerization zone will normally be at least about 85 percent. It is preferred for the monomer conversion to be at least about 90 percent.

The polymerization will be initiated with an anionic initiator, such as an alkyl lithium compound, or a Zeigler-Natta catalyst. The alkyl lithium compounds that can be used will typically contain from 1 to about 8 carbon atoms, and will preferably contain from 2 to 6 carbon atoms. The alkyl lithium initiator will preferably be n-butyl lithium.

The amount of the lithium initiator utilized will vary with the monomers being polymerized and with the molecular weight that is desired for the polymer being synthesized. However, as a general rule, from 0.01 to 1 phm (parts per 100 parts by weight of monomer) of the lithium initiator will be utilized. In most cases, from 0.01 to 0.1 phm of the lithium initiator will be utilized with it being preferred to utilize 0.025 to 0.07 phm of the lithium initiator.

The polymerization process of this invention is normally conducted in the presence of polar modifiers, such as alkyltetrahydrofurfuryl ethers. Some representative examples of specific polar modifiers that can be used include methyltetrahydrofurfuryl ether, ethyltetrahydrofurfuryl ether, propyltetrahydrofurfuryl ether, butyltetrahydrofurfuryl ether, hexyltetrahydrofurfuryl ether, octyltetrahydrofurfuryl ether, dodecyltetrahydrofurfuryl ether, diethyl ether, di-n-propyl ether, diisopropyl ether, di-n-butyl ether, tetrahydrofuran, dioxane, ethylene glycol dimethyl ether, ethylene glycol diethyl ether, diethylene glycol dimethyl ether, diethylene glycol diethyl ether, triethylene glycol dimethyl ether, trimethylamine, triethylamine, N,N,N',N'-tetramethylethylenediamine, N-methyl morpholine, N-ethyl morpholine, or N-phenyl morpholine.

The polar modifier will typically be employed at a level wherein the molar ratio of the polar modifier to the lithium initiator is within the range of about 0.01:1 to about 5:1. The molar ratio of the polar modifier to the lithium initiator will more typically be within the range of about 0.1:1 to about 4:1. It is generally preferred for the molar ratio of polar modifier to the lithium initiator to be within the range of about 0.25:1 to about 3:1. It is generally most preferred for the molar ratio of polar modifier to the lithium initiator to be within the range of about 0.5:1 to about 3:2.

The polymerization can optionally be conducted utilizing an oligomeric oxolanyl alkane as the modifier. Such oligomeric oxolanyl alkanes will typically be of a structural formula selected from the group consisting of:

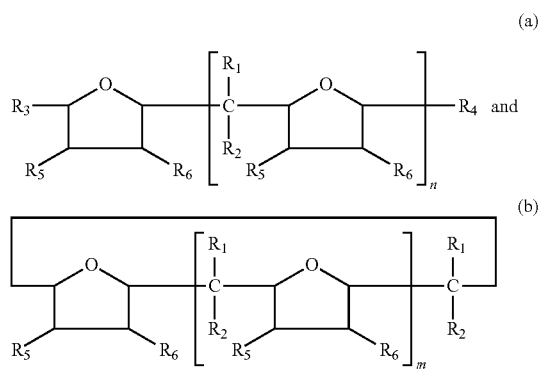

wherein n represents an integer from 1 to 5, wherein m represents an integer from 3 to 5, wherein $R_1$, $R_2$, $R_3$, $R_4$, $R_5$, and $R_6$ can be the same or different, and wherein $R_1$, $R_2$, $R_3$, $R_4$, $R_5$, and $R^6$ represent a member selected from the group consisting of hydrogen atoms and alkyl groups containing from 1 to about 8 carbon atoms. It is typically preferred for $R_1$, $R_2$, $R_3$, $R^4$, $R_5$, and $R^6$ represent a member selected from the group consisting of hydrogen atoms and alkyl groups containing from 1 to 4 carbon atoms.

The polymerization will also be conducted in the presence of an alkali metal alkoxide. The alkali metal alkoxide employed will typically be of the structural formula: M-O—R wherein M represents an alkali metal and wherein R represents an alkyl group (including cycloalkyl groups), an aryl group, an alkaryl group, or an arylalkyl group. The alkali metal will normally be a metal from Group I of the Periodic Table with lithium, sodium and potassium being preferred. Some representative examples of alkali metal alkoxides that can be used include: lithium methoxide, lithium ethoxide, lithium isopropoxide, lithium n-butoxide, lithium sec-butoxide, lithium t-butoxide, lithium 1,1-dimethylpropoxide, lithium 1,2-dimethylpropoxide, lithium 1,1-dimethylbutoxide, lithium 1,10-dimethylpentoxide, lithium 2-ethylhexanoxide, lithium 1-methylheptoxide, lithium phenoxide, lithium p-methylphenoxide, lithium p-octylphenoxide, lithium p-nonylphenoxide, lithium p-dodecylphenoxide, lithium α-naphthoxide, lithium β-naphthoxide, lithium o-methoxyphenoxide, lithium o-metnoxyphenoxide, lithium m-methoxyphenoxide, lithium p-methoxyphenoxide, lithium o-ethoxyphenoxide, lithium 4-methoxy-1-naphthoxide, sodium methoxide, sodium ethoxide, sodium isopropoxide, sodium n-butoxide, sodium sec-butoxide, sodium t-butoxide, sodium 1,1-dimethylpropoxide, sodium 1,2-dimethylpropoxide, sodium 1,1-dimethylbutoxide, sodium 1,10-dimethylpentoxide, sodium 2-ethylhexanoxide, sodium 1-methylheptoxide, sodium phenoxide, sodium p-methylphenoxide, sodium p-octylphenoxide, sodium p-nonylphenoxide, sodium p-dodecylphenoxide, sodium α-naphthoxide, sodium β-naphthoxide, sodium o-methoxyphenoxide, sodium o-metnoxyphenoxide, sodium m-methoxyphenoxide, sodium p-methoxyphenoxide, sodium o-ethoxyphenoxide, sodium 4-methoxy-1-naphthoxide, potassium methoxide, potassium ethoxide, potassium isopropoxide, potassium n-butoxide, potassium sec-butoxide, potassium t-butoxide, potassium 1,1-dimethylpropoxide, potassium 1,2-dimethylpropoxide, potassium 1,1-dimethylbutoxide, potassium 1,10-dimethylpentoxide, potassium 2-ethylhexanoxide, potassium 1-methylheptoxide, potassium phenoxide, potassium p-methylphenoxide, potassium p-octylphenoxide, potassium p-nonylphenoxide, potassium p-dodecylphenoxide, potassium α-naphthoxide, potassium β-naphthoxide, potassium o-methoxyphenoxide, potassium o-metnoxyphenoxide, potassium m-methoxyphenoxide, potassium p-methoxyphenoxide, potassium o-ethoxyphenoxide, potassium 4-methoxy-1-naphthoxide, and the like.

It is preferred for the alkali metal alkoxide to be an alkali metal salt of a cyclic alcohol. The metal salt of the cyclic alcohol will typically be a Group Ia metal salt. Lithium, sodium, potassium, rubidium, and cesium salts are representative examples of such salts with lithium, sodium, and potassium salts being preferred. Sodium salts are typically the most preferred. The cyclic alcohol can be mono-cyclic, bi-cyclic or tri-cyclic and can be aliphatic or aromatic. They can be substituted with 1 to 5 hydrocarbon moieties and can also optionally contain hetero-atoms. For instance, the metal salt of the cyclic alcohol can be a metal salt of a di-alkylated cyclohexanol, such as 2-isopropyl-5-methylcyclohexanol or 2-t-butyl-5-methylcyclohexanol. These salts are preferred because they are soluble in hexane. Metal salts of disubstituted cyclohexanol are highly preferred because they are soluble in hexane and provide similar modification efficiencies to sodium t-amylate. Sodium mentholate is the most highly preferred metal salt of a cyclic alcohol that can be employed in the practice of this invention. Metal salts of thymol can also be utilized. The metal salt of the cyclic alcohol can be prepared by reacting the cyclic alcohol directly with the metal or another metal source, such as sodium hydride, in an aliphatic or aromatic solvent. Some representative examples of alcohols which can be utilized in preparing the lithium alkoxide include t-butanol, sec-butanol, cyclohexanol, octanol, 2-ethylhexanol, p-cresol, m-cresol, nonylphenol, hexylphenol, tetrahydrofuryl alcohol, furfuryl alcohol, and tetrahydrofurfuryl, and the like.

The molar ratio of the alkali metal alkoxide to the lithium initiator will typically be within the range of about 0.001:1 to about 2:1. The molar ratio of the alkali metal alkoxide to the lithium initiator will more typically be within the range of about 0.005:1 to about 1:1. The molar ratio of the alkali metal alkoxide to the lithium initiator will preferably be within the range of about 0.008:1 to about 0.3:1.

The polymerization temperature utilized can vary over a broad range of from about −20° C. to about 180° C. In most cases, a polymerization temperature within the range of about 30° C. to about 125° C. will be utilized. It is typically preferred for the polymerization temperature to be within the range of about 45° C. to about 100° C. It is typically most preferred for the polymerization temperature to be within the range of about 60° C. to about 90° C. The pressure used will normally be sufficient to maintain a substantially liquid phase under the conditions of the polymerization reaction.

The polymerization is conducted for a length of time sufficient to permit substantially complete polymerization of monomers. In other words, the polymerization is normally carried out until high conversions of at least about 85 percent are attained. The polymerization is then terminated by the addition of an agent, such as an alcohol, a terminating agent, or a coupling agent. This inherently results in the rubbery polymer having a monomodal molecular weight distribution. For example, a tin halide and/or silicon halide can be used as a coupling agent. The tin halide and/or the silicon halide are continuously added in cases where asymmetrical coupling is desired. This continuous addition of tin coupling agent and/or the silicon coupling agent is normally done in a reaction zone separate from the zone where the bulk of the polymerization is occurring. The coupling agents will normally be added in a separate reaction vessel after the desired degree of conversion has been attained. The coupling agents can be added in a hydrocarbon solution, e.g., in cyclohexane, to the polymerization admixture with suitable mixing for distribution and reaction. In other words, the coupling will typically be added only after a high degree of conversion has already been attained. For instance, the coupling agent will normally be added only after a monomer conversion of greater than about 85 percent has been realized. It will typically be preferred for the monomer conversion to reach at least about 90 percent before the coupling agent is added.

The tin halides used as coupling agents will normally be tin tetrahalides, such as tin tetrachloride, tin tetrabromide, tin tetrafluoride or tin tetraiodide. However, tin trihalides can also optionally be used. Polymers coupled with tin trihalides have a maximum of three arms. This is, of course, in contrast to polymers coupled with tin tetrahalides which have a maximum of four arms. To induce a higher level of branching, tin tetrahalides are normally preferred. As a general rule, tin tetrachloride is most preferred.

The silicon halides that can be used as coupling agents will normally be silicon tetrahalides, such as silicon tetrachloride, silicon tetrabromide, silicon tetrafluoride or silicon tetraiodide. However, silicon trihalides can also optionally be used. Polymers coupled with silicon trihalides have a maximum of three arms. This is, of course, in contrast to polymers coupled with silicon tetrahalides which have a maximum of four arms. To induce a higher level of branching, silicon tetrahalides are normally preferred. As a general rule, silicon tetrachloride is the most preferred of the silicon coupling agents.

A combination of a tin halide and a silicon halide can optionally be used to couple the rubbery polymer. By using such a combination of tin and silicon coupling agents improved properties for tire rubbers, such as lower hysteresis, can be attained. It is particularly desirable to utilize a combination of tin and silicon coupling agents in tire tread compounds that contain both silica and carbon black. In such cases, the molar ratio of the tin halide to the silicon halide employed in coupling the rubbery polymer will normally be within the range of 20:80 to 95:5. The molar ratio of the tin halide to the silicon halide employed in coupling the rubbery polymer will more typically be within the range of 40:60 to 90:10. The molar ratio of the tin halide to the silicon halide employed in coupling the rubbery polymer will preferably be within the range of 60:40 to 85:15. The molar ratio of the tin halide to the silicon halide employed in coupling the rubbery polymer will most preferably be within the range of 65:35 to 80:20.

Broadly, and exemplary, a range of about 0.01 to 4.5 milliequivalents of tin coupling agent (tin halide and silicon halide) is employed per 100 grams of the rubbery polymer. It is normally preferred to utilize about 0.01 to about 1.5 milliequivalents of the coupling agent per 100 grams of polymer to obtain the desired Mooney viscosity. The larger quantities tend to result in production of polymers containing terminally reactive groups or insufficient coupling. One equivalent of tin coupling agent per equivalent of lithium is considered an optimum amount for maximum branching. For instance, if a mixture of tin tetrahalide and silicon tetrahalide is used as the coupling agent, one mole of the coupling agent would be utilized per four moles of live lithium ends. In cases where a mixture of tin trihalide and silicon trihalide is used as the coupling agent, one mole of the coupling agent will optimally be utilized for every three moles of live lithium ends. The coupling agent can be added in a hydrocarbon solution, e.g., in cyclohexane, to the polymerization admixture in the reactor with suitable mixing for distribution and reaction.

After the coupling has been completed, a tertiary chelating alkyl 1,2-ethylene diamine or a metal salt of a cyclic alcohol can optionally be added to the polymer cement to stabilize the coupled rubbery polymer. The tertiary chelating amines that can be used are normally chelating alkyl diamines of the structural formula:

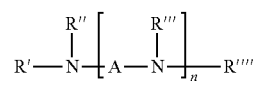

wherein n represents an integer from 1 to about 6, wherein A represents an alkylene group containing from 1 to about 6 carbon atoms and wherein R', R'', R''' and R'''' can be the same or different and represent alkyl groups containing from 1 to about 6 carbon atoms. The alkylene group A is of the formula —($-CH_2-$)$_m$ wherein m is an integer from 1 to about 6. The alkylene group will typically contain from 1 to 4 carbon atoms (m will be 1 to 4) and will preferably contain 2 carbon atoms. In most cases, n will be an integer from 1 to about 3 with it being preferred for n to be 1. It is preferred for R', R", R''' and R'''' to represent alkyl groups which contain from 1 to 3 carbon atoms. In most cases, R', R", R''' and R'''' will represent methyl groups.

In most cases, from about 0.01 phr (parts by weight per 100 parts by weight of dry rubber) to about 2 phr of the chelating alkyl 1,2-ethylene diamine or metal salt of the cyclic alcohol will be added to the polymer cement to stabilize the rubbery polymer. Typically, from about 0.05 phr to about 1 phr of the chelating alkyl 1,2-ethylene diamine or metal salt of the cyclic alcohol will be added. More typically, from about 0.1 phr to about 0.6 phr of the chelating alkyl 1,2-ethylene diamine or the metal salt of the cyclic alcohol will be added to the polymer cement to stabilize the rubbery polymer.

The terminating agents that can be used to stop the polymerization and to "terminate" the living rubbery polymer include tin monohalides, silicon monohalides, N,N,N', N'-tetradialkyldiamino-benzophenones (such as tetramethyldiaminobenzophenone and the like), N,N-dialkylaminobenzaldehydes (such as dimethylaminobenzaldehyde and the like), 1,3-dialkyl-2-imidazolidinones (such as 1,3-dimethyl-2-imidazolidinone and the like), 1-alkyl substituted pyrrolidinones; 1-aryl substituted pyrrolidinones, dialkyl-dicycloalkyl-carbodiimides containing from about 5 to about 20 carbon atoms, and dicycloalkyl-carbodiimides containing from about 5 to about 20 carbon atoms.

After the termination step, and optionally the stabilization step, has been completed, the rubbery polymer can be recovered from the organic solvent. The coupled rubbery polymer can be recovered from the organic solvent and residue by means such as chemical (alcohol) coagulation, thermal desolventization, or other suitable method. For instance, it is often desirable to precipitate the rubbery polymer from the organic solvent by the addition of lower alcohols containing from about 1 to about 4 carbon atoms to the polymer solution. Suitable lower alcohols for precipitation of the rubber from the polymer cement include methanol, ethanol, isopropyl alcohol, normal-propyl alcohol and t-butyl alcohol. The utilization of lower alcohols to precipitate the rubbery polymer from the polymer cement also "terminates" any remaining living polymer by inactivating lithium end groups. After the coupled rubbery polymer is recovered from the solution, steam-stripping can be employed to reduce the level of volatile organic compounds in the coupled rubbery polymer. Additionally, the organic solvent can be removed from the rubbery polymer by drum drying, extruder drying, vacuum drying, and the like.

The polymers of the present invention can be used alone or in combination with other elastomers to prepare rubber compounds, such as a tire treadstock, sidewall stock or other tire component stock compounds. In a tire of the invention, at least one such component is produced from a vulcanizable elastomeric or rubber composition. For example, the rubbery polymer made by the process of this invention can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, Neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like.

When the rubbery polymers made by the process of the present invention are blended with conventional rubbers, the amounts can vary widely such as between 10 and 99 percent by weight. In any case, tires made with synthetic rubbers that are synthesized utilizing the technique of this invention exhibit decreased rolling resistance. The greatest benefits are realized in cases where the tire tread compound is made with the rubbery polymer synthesized utilizing the technique of this invention. However, benefits can also by attained in cases where at least one structural element of the tire, such as the subtread, sidewalls, body ply skim, or bead filler, is comprised of the rubbery polymer.

The synthetic rubbers made in accordance with this invention can be compounded with carbon black in amounts ranging from about 5 to about 100 phr (parts by weight per 100 parts by weight of rubber), with about 5 to about 80 phr being preferred, and with about 40 to about 70 phr being more preferred. The carbon blacks may include any of the commonly available, commercially-produced carbon blacks but those having a surface area (EMSA) of at least 20 $m^2/g$ and more preferably at least 35 $m^2/g$ up to 200 $m^2/g$ or higher are preferred. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention. Typical values for surface areas of usable carbon blacks are summarized in the following table.

| Carbon Black | |
|---|---|
| ASTM Designation (D-1765-82a) | Surface Area (D-3765) |
| N-110 | 126 $m^2/g$ |
| N-220 | 111 $m^2/g$ |
| N-330 | 83 $m^2/g$ |
| N-339 | 95 $m^2/g$ |
| N-550 | 42 $m^2/g$ |
| N-660 | 35 $m^2/g$ |

The carbon blacks utilized in the preparation of rubber compounds may be in pelletized form or an unpelletized flocculent mass. Preferably, for more uniform mixing, unpelletized carbon black is preferred. The reinforced rubber compounds can be cured in a conventional manner with about 0.5 to about 4 phr of known vulcanizing agents. For example, sulfur or peroxide-based curing systems may be employed. For a general disclosure of suitable vulcanizing agents one can refer to Kirk-Othmer, Encyclopedia of Chemical Technology, 3rd ed., Wiley Interscience, N.Y. 1982, Vol. 20, pp. 365-468, particularly "Vulcanization Agents and Auxiliary Materials" pp. 390-402. Vulcanizing agents can, of course, be used alone or in combination. Vulcanizable elastomeric or rubber compositions can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

The functionalized rubbery polymers of this invention can be compounded utilizing conventional ingredients and standard techniques. For instance, the functionalized rubbery polymers of this invention will typically be blended with carbon black, sulfur, fillers, accelerators, oils, waxes, scorch inhibiting agents, and processing aids. In most cases, the functionalized rubbery polymer will be compounded with sulfur and/or a sulfur containing compound, at least one filler, at least one accelerator, at least one antidegradant, at least one processing oil, zinc oxide, optionally a tackifier resin, optionally a reinforcing resin, optionally one or more fatty acids, optionally a peptizer and optionally one or more scorch inhibiting agents. Such blends will normally contain from about 0.5 to 5 phr (parts per hundred parts of rubber by weight) of sulfur and/or a sulfur containing compound with 1 phr to 2.5 phr being preferred. It may be desirable to utilize insoluble sulfur in cases where bloom is a problem.

Normally from 10 phr to 150 phr of at least one filler will be utilized in the blend with 30 phr to 80 phr being preferred. In most cases at least some carbon black will be utilized in the filler. The filler can, of course, be comprised totally of carbon black. Silica can be included in the filler to improve tear resistance and heat build up. Clays and/or talc can be included in the filler to reduce cost. The blend will also normally include from 0.1 to 2.5 phr of at least one accelerator with 0.2 to 1.5 phr being preferred. Antidegradants, such as antioxidants and antiozonants, will generally be included in the blend in amounts ranging from 0.25 to 10 phr with amounts in the range of 1 to 5 phr being preferred. Processing oils will generally be included in the blend in amounts ranging from 2 to 100 phr with amounts ranging from 5 to 50 phr being preferred. The functionalized rubbery polymers of this invention will also normally contain from 0.5 to 10 phr of zinc oxide with 1 to 5 phr being preferred. These blends can optionally contain from 0 to 10 phr of tackifier resins, 0 to 10 phr of reinforcing resins, 1 to 10 phr of fatty acids, 0 to 2.5 phr of peptizers, and 0 to 1 phr of scorch inhibiting agents.

To fully realize the total advantages of the functionalized rubbery polymers of this invention in tire tread formulations, silica will normally be included in the tread rubber formulation. The processing of the functionalized rubbery polymers blend is normally conducted in the presence of a silica coupling agent (sulfur containing organosilicon compound) to realize maximum benefits. Some representative examples of suitable sulfur containing organosilicon compounds that can be employed as the silica coupling agent are of the formula:

$$Z\text{-Alk-}S_n\text{-Alk-}Z \qquad (I)$$

in which Z is selected from the group consisting of

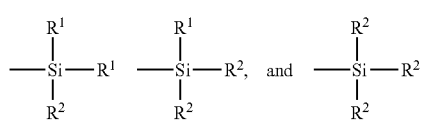

where $R^1$ is an alkyl group of 1 to 4 carbon atoms, cyclohexyl or phenyl; wherein $R^2$ is alkoxy of 1 to 8 carbon atoms, or cycloalkoxy of 5 to 8 carbon atoms; and wherein Alk is a divalent hydrocarbon of 1 to 18 carbon atoms and n is an integer of 2 to 8.

Specific examples of sulfur containing organosilicon compounds which may be used as the silica coupling agent in accordance with the present invention include: 3,3'-bis(trimethoxysilylpropyl) disulfide, 3,3'-bis(triethoxysilylpropyl) tetrasulfide, 3,3'-bis(triethoxysilylpropyl) octasulfide, 3,3'-bis(trimethoxysilylpropyl) tetrasulfide, 2,2'-bis(triethoxysilylethyl) tetrasulfide, 3,3'-bis(trimethoxysilylpropyl) trisulfide, 3,3'-bis(triethoxysilylpropyl) trisulfide, 3,3'-bis(tributoxysilylpropyl) disulfide, 3,3'-bis(trimethoxysilylpropyl) hexasulfide, 3,3'-bis(trimethoxysilylpropyl) octasulfide, 3,3'-bis(trioctoxysilylpropyl) tetrasulfide, 3,3'-bis(trihexoxysilylpropyl) disulfide, 3,3'-bis(tri-2"-ethylhexoxysilylpropyl) trisulfide, 3,3'-bis(triisooctoxysilylpropyl) tetrasulfide, 3,3'-bis(tri-t-butoxysilylpropyl) disulfide, 2,2'-bis(methoxydiethoxysilylethyl) tetrasulfide, 2,2'-bis(tripropoxysilylethyl) pentasulfide, 3,3'-bis(tricyclonexoxysilylpropyl) tetrasulfide, 3,3'-bis(tricyclopentoxysilylpropyl) trisulfide, 2,2'-bis(tri-2"-methylcyclohexoxysilylethyl) tetrasulfide, bis(trimethoxysilylmethyl) tetrasulfide, 3-methoxy ethoxy propoxysilyl 3'-diethoxybutoxysilylpropyltetrasulfide, 2,2'-bis(dimethyl methoxysilylethyl) disulfide, 2,2'-bis(dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'-bis(diphenyl isopropoxysilylpropyl) tetrasulfide, 3,3'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3'-bis(diethyl methoxysilylpropyl) tetrasulfide, 3,3'-bis(ethyl di-sec. butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3'-trimethoxysilylpropyl tetrasulfide, 4,4'-bis(trimethoxysilylbutyl) tetrasulfide, 6,6'-bis(triethoxysilylhexyl) tetrasulfide, 12,12'-bis(triisopropoxysilyl dodecyl) disulfide, 18,18'-bis(trimethoxysilyloctadecyl) tetrasulfide, 18,18'-bis(tripropoxysilyloctadecenyl) tetrasulfide, 4,4'-bis(trimethoxysilyl-buten-2-yl) tetrasulfide, 4,4'-bis(trimethoxysilylcyclohexylene) tetrasulfide, 5,5'-bis(dimethoxymethylsilylpentyl) trisulfide, 3,3'-bis(trimethoxysilyl-2-methylpropyl) tetrasulfide, 3,3'-bis(dimethoxyphenylsilyl-2-methylpropyl) disulfide.

The preferred sulfur containing organosilicon compounds are the 3,3'-bis(trimethoxy or triethoxy silylpropyl) sulfides. The most preferred compound is 3,3'-bis(triethoxysilylpropyl) tetrasulfide. Therefore as to formula I, preferably Z is

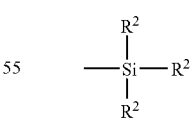

where $R^2$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 3 to 5 with 4 being particularly preferred.

The utilization of the functionalized polymers of this invention in silica filler rubber compounds can totally eliminate the need for silica coupling agents. Accordingly, the rubbery compositions of this invention can be totally void of silica coupling agents. However, a small amount of a silica coupling agent can optionally be used. The amount of a sulfur containing organosilicon compound of formula I that is optionally utilized in the rubber compositions of this invention as a silica coupling agent will vary depending on the level of silica that is used. However, the level of silica coupling agent needed is greatly reduced from the level that is typically employed in conventional silica filler rubber formulations. This reduces the cost of the rubber compound significantly since the silica coupling agent is normally one of the most expensive raw materials employed in tire rubber compounds. In any case, the level of silica coupling agent utilized in the rubbery compositions of this invention will be less than 5 phr. The amount of silica coupling agent used will more typically be within the range of about 0.5 phr to about 4 phr and will preferably be within the range of 1 phr to 2 phr.

The silica filler may be added in amounts ranging from about 10 phr to about 250 phr. Preferably, the silica is present in an amount ranging from about 15 phr to about 80 phr. If carbon black is also present, the amount of carbon black, if used, may vary. Generally speaking, the amount of carbon black will vary from about 5 phr to about 80 phr. Preferably, the amount of carbon black will range from about 10 phr to about 40 phr. It is to be appreciated that the silica coupler may be used in conjunction with a carbon black, namely pre-mixed with a carbon black prior to addition to the rubber composition, and such carbon black is to be included in the aforesaid amount of carbon black for the rubber composition formulation. In any case, the total quantity of silica and carbon black will be at least about 30 phr. The combined weight of the silica and carbon black, as hereinbefore referenced, may be as low as about 30 phr, but is preferably from about 45 to about 130 phr.

The commonly employed siliceous pigments used in rubber compounding applications can be used as the silica. For instance the silica can include pyrogenic and precipitated siliceous pigments (silica), although precipitate silicas are preferred. The siliceous pigments preferably employed in this invention are precipitated silicas such as, for example, those obtained by the acidification of a soluble silicate, e.g., sodium silicate.

Such silicas might be characterized, for example, by having a BET surface area, as measured using nitrogen gas, preferably in the range of about 40 to about 600, and more usually in a range of about 50 to about 300 square meters per gram. The BET method of measuring surface area is described in the Journal of the American Chemical Society, Volume 60, page 304 (1930).

The silica may also be typically characterized by having a dibutylphthalate (DBP) absorption value in a range of about 100 to about 400, and more usually about 150 to about 300. The silica might be expected to have an average ultimate particle size, for example, in the range of 0.01 to 0.05 micron as determined by the electron microscope, although the silica particles may be even smaller, or possibly larger, in size.

Various commercially available silicas may be considered for use in this invention such as, only for example herein, and without limitation, silicas commercially available from PPG Industries under the Hi-Sil trademark with designations 210, 243, etc; silicas available from Rhone-Poulenc, with, for example, designations of Z1165MP and Z165GR and silicas available from Degussa AG with, for example, designations VN2 and VN3.

It is particularly desirable to include lignin in silica filled tire tread formulations. Lignin further improves filler/polymer compatibility and reduces the overall weight of the tire tread formulation. The lignin can be a lignosulfonate (also called lignin sulfonate and sulfite lignin) or a kraft lignin (also called sulfate lignin). The lignin will typically be included in the tire tread formulation at an amount which is within the range of 10 phr to 80 phr and will more typically be present at an amount which is within the range of 15 phr to 30 phr. Starch can also beneficially be utilized as a filler in such compositions in addition to the lignin at an amount which is within the range of 10 phr to 50 phr and which is more typically within the range of 15 phr to 30 phr.

Tire tread formulations which include silica and an organosilicon compound will typically be mixed utilizing a thermomechanical mixing technique. The mixing of the tire tread rubber formulation can be accomplished by methods known to those having skill in the rubber mixing art. For example the ingredients are typically mixed in at least two stages, namely at least one non-productive stage followed by a productive mix stage. The final curatives including sulfur vulcanizing agents are typically mixed in the final stage which is conventionally called the "productive" mix stage in which the mixing typically occurs at a temperature, or ultimate temperature, lower than the mix temperature(s) than the preceding non-procuctive mix stage(s). The rubber, silica and sulfur containing organosilicon, and carbon black if used, are mixed in one or more non-productive mix stages. The terms "non-productive" and "productive" mix stages are well known to those having skill in the rubber mixing art.

The sulfur vulcanizable rubber composition containing the sulfur containing organosilicon compound, vulcanizable rubber and generally at least part of the silica should be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions and the volume and nature of the components. For example, the thermomechanical working may be for a duration of time which is within the range of about 2 minutes to about 20 minutes. It will normally be preferred for the rubber to reach a temperature which is within the range of about 145° C. to about 180° C. and to be maintained at said temperature for a period of time which is within the range of about 4 minutes to about 12 minutes. It will normally be more preferred for the rubber to reach a temperature which is within the range of about 155° C. to about 170° C. and to be maintained at said temperature for a period of time which is within the range of about 5 minutes to about 10 minutes.

The non-random rubbery polymer containing rubber blends of this invention can be used in tire treads in conjunction with ordinary tire manufacturing techniques. Tires are built utilizing standard procedures with the non-random rubbery polymer being blended with a polybutadiene rubber. As has been noted, it is preferred for such tire tread formulations to be filled with both silica and lignin. After the tire has been built with the non-random rubbery polymer containing blend, it can be vulcanized using a normal tire cure cycle. Tires made in accordance with this invention can be cured over a wide temperature range. However, it is generally preferred for the tires of this invention to be cured at a temperature ranging from about 132° C. (270° F.) to about 166° C. (330° F.). It is more typical for the tires of this invention to be cured at a temperature ranging from about 143° C. (290° F.) to about 154° C. (310° F.). It is generally preferred for the cure cycle used to vulcanize the tires of this invention to have a duration of about 10 to about 14 minutes with a cure cycle of about 12 minutes being most preferred.

The functionalized styrene monomer can be synthesized by (1) reacting a primary or secondary amine with an organolithium compound to produce a lithium amide, and (2) reacting the lithium amide with divinylbenzene or diisopropenyl benzene to produce the functionalized styrene monomer. It is preferred to utilize a secondary amine in the first step. This procedure can be depicted as follows:

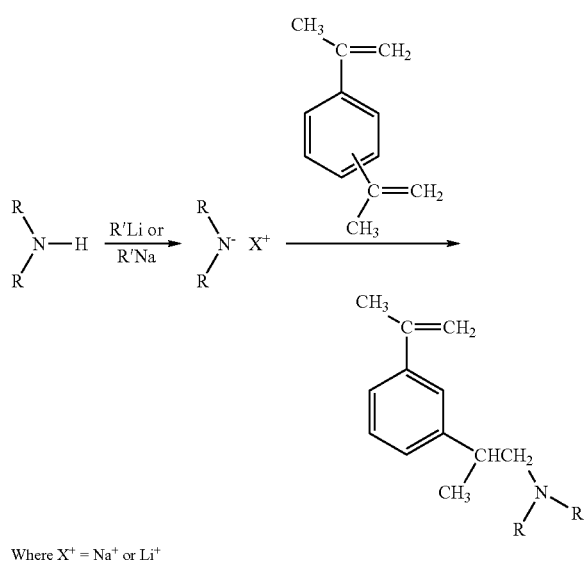

Where X$^+$ = Na$^+$ or Li$^+$

In the reaction scheme shown above, the R groups represent hydrogen atoms or alkyl moieties containing from 1 to about 8 carbon atoms and the R' groups represent alkyl moieties containing from 1 to about 8 carbon atoms. It is preferred for R' to represent an alkyl moiety containing from 3 to 6 carbon atoms, such as an n-butyl group. It should be noted that the R groups can be the same or different with it being preferred for one of the R groups to represent a hydrogen atom with the other R group representing an alkyl moiety.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLES 1-5

In this series of experiments, 3,4-(2-N-alkylaminoethyl) styrene was prepared by the addition of the appropriate primary or secondary amine to a mixture of divinyl benzene in hexane solution the presence of n-butyl-lithium at 10° C.

In Example 1, 3,4-(2-N-butylaminoethyl) styrene was prepared using the general procedure described above. In the procedure used, one mole of divinyl benzene (60/40 mixture of both the para and meta isomers) and one mole of butyl amine in two liters of hexane solvent was added to a three neck flask equipped with an air driven motor under a nitrogen atmosphere. This solution was cooled to 10° C. and then 30 mmoles of butyl-lithium was added. The solution turned reddish in color. After one hour of reaction time the solvent was evaporated under a rotary vacuum to remove all of the hexane solvent. The residue was distilled under vacuum and the product that was isolated was determined to be a mixture of the 3,4-(2-N-butylaminoethyl) styrene.

In the next experiment (Example 2), 3,4-(2-aminoethyl) styrene was synthesized using the same general procedure. In the procedure used, one mole of divinyl benzene (60/40 mixture of both the para and meta isomers) in two liters of hexane solvent was added to a three neck flask equipped with an air driven motor under a nitrogen atmosphere. Then 1 mole of anhydrous ammonia was added and the solution was cooled to 10° C. and then 30 mmoles of n-butyl-lithium was added. After one hour of reaction time the mixture was distilled and then the solvent was evaporated under a rotary vacuum. The product that was isolated was determined by C$_{13}$NMR to be a mixture of the 3,4-(2-aminoethyl) styrene.

In another experiment (Example 3), 3,4-(2-aminoethyl) styrene was again prepared utilizing the same general procedure. In the procedure used, one mole of divinyl benzene (60/40 mixture of both the para and meta isomers) in two liters of tetrahydrofuran was added to a three neck flask equipped with an air driven motor under a nitrogen atmosphere. Then 1 mole of sodium amide was added and the solution was cooled to 10° C. and then 30 mmoles of n-butyl-lithium was added. After one hour of reaction time the solution was neutralized with sodium carbonate and the solution was distilled under vacuum. Then the tetrahydrofuran solvent was removed by evaporation under a rotary vacuum. The product that was isolated was determined to be 3,4-(2-aminoethyl) styrene.

In another experiment (Example 4), 3,4-(2-aminoethyl) styrene was again prepared utilizing the same general procedure. In the procedure used, one mole of divinyl benzene (60/40 mixture of both the para and meta isomers) in two liters of tetrahydrofuran was added to a three neck flask equipped with an air driven motor under a nitrogen atmosphere. Then 1 mole of lithium amide was added and the solution was cooled to 10° C. and then 30 mmoles of n-butyl-lithium was added. After one hour of reaction time the solution was neutralized with sodium carbonate and the solution was distilled under vacuum. Then the tetrahydrofuran solvent was removed by evaporation under a rotary vacuum. The product that was isolated was determined to be 3,4-(2-aminoethyl) styrene.

In the next experiment (Example 5), 3,4-(2-N-methylaminoethyl) styrene was prepared utilizing the same general procedure. In the procedure used, one mole of divinyl benzene (60/40 mixture of both the para and meta isomers) in two liters of hexane solvent was added to a three neck flask equipped with an air driven motor under a nitrogen atmosphere. Then 1 mole of methylamine was added and the solution was cooled to 10° C. and then 30 mmoles of n-butyl-lithium was added. After one hour of reaction time the mixture was distilled and then the solvent was evaporated under a rotary vacuum. The product that was isolated was determined by C$_{13}$ NMR to be a mixture of the 3,4-(2-N-methylaminoethyl) styrene.

EXAMPLE 6

In this experiment, the amine group on 3,4-(2-N-methyl-aminoethyl) styrene monomer was protected with chlorotrimetylsilane so that it could be polymerized with anionic initiators under solution polymerization conditions. In the procedure used a three neck flask was charged with one liter of hexane and one mole of the 3,4-(2-aminoethyl) styrene monomer synthesized in Example 2 and cooled to room temperature. Then, two moles of trimethychlorosilane was added drop wise at a very slow rate to the mixture. After the addition was completed the reaction mixture was neutralized with sodium carbonate. The hexane solvent was removed and the residue was vacuumed distilled. The resulting product was identified by $C_{13}$ NMR as the 3,4-(2-N,N-di-trimethylsilylaminoethyl) styrene. This monomer having protected amine groups could then be used in anionic polymerizations.

EXAMPLE 7

A styrene butadiene rubber which is functionalized with 3,4-(2-aminoethyl) styrene monomer can be prepared by anionic solution polymerization by charging 2350 g of a silica/alumina/molecular sieve dried premix containing 19.50 weight percent styrene and 1,3-butadiene in hexanes into a one-gallon (3.8 liters) reactor. In such a polymerization, 4.6 grams of a neat 3,4-(2-N,N-di-trimethylsilylaminoethyl) styrene can be charged into the reactor which contains the styrene and butadiene monomers. Then, 2.9 ml of 1 M solution of N,N,N',N'-tetramethyethylenediamine (TMEDA) and 2.3 ml of 1.6 M n-butyl lithium (n-BuLi) in hexanes were added to the reactor, respectively. Such a polymerization can be carried out at 70° C. for 90 minutes. All available monomer was consumed at which time, and then, ethanol was added to shortstop the polymerization. The functionalized styrene butadiene rubber can then be removed from the reactor and stabilized with 1 phm of antioxidant. After evaporating hexanes solvent, the resulting polymer can be dried in a vacuum oven at 50° C. The protected amine groups on the 3,4-(2-N,N-di-trimethylsilyl aminoethyl) styrene monomer was deprotected to form 3,4-(2-aminoethyl) styrene during the recovery of the polymer from the solution.

EXAMPLE 8

In this procedure the same technique as was described in Example 7 can be repeated except with the 3,4-(2-N,N-di-trimethylsilylaminoethyl) styrene monomer being premixed with the styrene and butadiene monomers prior to being charged into the reactor. Such a procedure will result in a high level of monomer conversion and the functionalized styrene butadiene rubber made can be recovered as described in Example 7.

While certain representative embodiments and details have been shown for the purpose of illustrating the subject invention, it will be apparent to those skilled in this art that various changes and modifications can be made therein without departing from the scope of the subject invention.

What is claimed is:

1. A rubbery composition which is comprised of (A) a silica filler, (B) optionally, a silica coupling agent, wherein the silica coupling agent is present at a maximum level of less than 5 phr, and (C) a rubbery polymer which is comprised of repeat units that are derived from (1) at least one conjugated diolefin monomer, and (2) from 0.1 phm to 5 phm of a functionalized monomer having the structural formula:

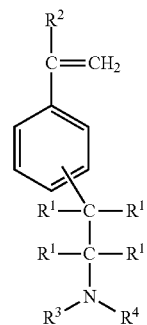

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom, wherein the repeat units that are derived from the functionalized monomer are distributed throughout the rubber polymer in an essentially random manner, wherein the rubbery polymer is not coupled, and wherein the rubbery polymer has a monomodal molecular weight distribution.

2. A rubbery composition as specified in claim 1 wherein the rubbery polymer is void of repeat units that are derived from vinyl aromatic compounds in addition to the functionalized monomer.

3. A rubbery composition as specified in claim 1 wherein the terminating agent is selected from the group consisting of tin monohalides, silicon monohalides, methanol, ethanol, isopropyl alcohol, normal-propyl alcohol, and t-butyl alcohol.

4. A tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is comprised of the rubbery composition specified in claim 1.

5. A tire as specified in claim 4 wherein the filler is silica and wherein said tread is void of silica coupling agents.

6. A rubbery composition which is comprised of (A) a silica filler, (B) optionally, a silica coupling agent, wherein the silica coupling agent is present at a maximum level of less than 5 phr, and (C) a rubbery polymer which is comprised of repeat units that are derived from (1) at least one conjugated diolefin monomer, and (2) from 0.1 phm to 5 phm of a functionalized monomer having the structural formula:

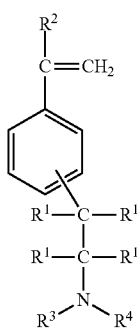

wherein the $R^1$ groups can be the same or different and represent hydrogen atoms or alkyl groups containing from 1 to about 8 carbon atoms, wherein $R^2$ represents a hydrogen atom or an alkyl group containing from 1 to about 8 carbon atoms, wherein $R^3$ represents a hydrogen atom or an alkyl group containing from 1 to about 8 carbon atoms, and wherein $R^4$ represents a hydrogen atom or an alkyl group containing from 1 to about 8 carbon atoms, with the proviso that if $R^3$ represent an alkyl group then $R^4$ represents a hydrogen atom, and with the proviso that $R^4$ represents an alkyl group then $R^3$ represents a hydrogen atom, wherein the repeat units that are derived from the functionalized monomer are distributed throughout the rubber polymer in an essentially random manner, wherein the rubbery polymer is not coupled, wherein the rubbery polymer has a monomodal molecular weight distribution, and wherein the rubbery polymer is made by a polymerization which is terminated after a conversion of at least 85 percent is attained.

7. A rubbery composition as specified in claim 6 wherein the rubbery polymer is void of repeat units that are derived from vinyl aromatic compounds in addition to the functionalized monomer.

8. A rubbery composition as specified in claim 6 wherein the terminating agent is selected from the group consisting of tin monohalides, silicon monohalides, methanol, ethanol, isopropyl alcohol, normal-propyl alcohol, and t-butyl alcohol.

9. A tire which is comprised of a generally toroidal-shaped carcass with an outer circumferential tread, two spaced beads, at least one ply extending from bead to bead and sidewalls extending radially from and connecting said tread to said beads, wherein said tread is adapted to be ground-contacting, and wherein said tread is comprised of the rubbery composition specified in claim 6.

10. A tire as specified in claim 9 wherein the filler is silica and wherein said tread is void of silica coupling agents.

* * * * *